(12) United States Patent
Kamei et al.

(10) Patent No.: US 12,399,103 B2
(45) Date of Patent: Aug. 26, 2025

(54) CELL LIFE-AND-DEATH DETERMINATION METHOD, CELL LIFE-AND-DEATH DETERMINATION DEVICE, AND CELL LIFE-AND-DEATH DETERMINATION SYSTEM

(71) Applicant: FUJIFILM Corporation, Tokyo (JP)

(72) Inventors: Shota Kamei, Kanagawa (JP); Takashi Morimoto, Kanagawa (JP); Tomoyuki Shimoda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 130 days.

(21) Appl. No.: 18/491,962

(22) Filed: Oct. 23, 2023

(65) Prior Publication Data

US 2024/0044773 A1    Feb. 8, 2024

Related U.S. Application Data

(63) Continuation of application No. PCT/JP2022/017730, filed on Apr. 13, 2022.

(30) Foreign Application Priority Data

Apr. 28, 2021  (JP) ................................ 2021-076026

(51) Int. Cl.
   *G01N 15/1434*   (2024.01)
   *B01L 3/00*      (2006.01)
   (Continued)

(52) U.S. Cl.
   CPC .... *G01N 15/1434* (2013.01); *B01L 3/502715* (2013.01); *G01N 15/1429* (2013.01);
   (Continued)

(58) Field of Classification Search
   CPC .............. G01N 15/01; G01N 15/1433; G01N 15/1468; G01N 2015/1006; G01N 2015/1452
   See application file for complete search history.

(56) References Cited

U.S. PATENT DOCUMENTS

| | | | |
|---|---|---|---|
| 2011/0261164 A1* | 10/2011 | Olesen ................... | G01N 17/00 382/128 |
| 2012/0013727 A1 | 1/2012 | Breniman et al. | |
| 2020/0257886 A1 | 8/2020 | Fujimoto et al. | |

FOREIGN PATENT DOCUMENTS

| | | |
|---|---|---|
| JP | 5-184579 A | 7/1993 |
| JP | 2013-517460 A | 5/2013 |

(Continued)

OTHER PUBLICATIONS

International Search Report dated Jul. 5, 2022 in Application No. PCT/JP2022/017730.

(Continued)

*Primary Examiner* — Thanh Luu
(74) *Attorney, Agent, or Firm* — Sughrue Mion, PLLC

(57) ABSTRACT

Provided are a cell life-and-death determination method, a cell life-and-death determination device, and a cell life-and-death determination system. The cell life-and-death determination method includes: acquiring images of a cell captured in a plurality of focal planes including an in-focus plane of the cell in a direction opposite to a side on which the cell is irradiated with light; acquiring an image piece including a central portion and an outer peripheral portion of the cell from each of the images; connecting the image pieces in an order of an imaging direction of the focal plane to create a connected image for analysis; extracting a feature amount from the connected image for analysis; and determining whether the cell is alive or dead on the basis of the (Continued)

feature amount of the connected image for analysis and a predetermined range of the feature amount.

15 Claims, 9 Drawing Sheets

(51) Int. Cl.
  *G01N 15/01* (2024.01)
  *G01N 15/1429* (2024.01)

(52) U.S. Cl.
  CPC . *B01L 2300/027* (2013.01); *B01L 2300/0654* (2013.01); *G01N 15/01* (2024.01)

(56) References Cited

FOREIGN PATENT DOCUMENTS

| JP | 2015-210212 A | 11/2015 |
| JP | 2016-192923 A | 11/2016 |
| WO | 2017/082048 A1 | 5/2017 |

OTHER PUBLICATIONS

International Preliminary Report on Patentability dated Oct. 24, 2023 with a Translation of the Written Opinion of the International Searching Authority in Application No. PCT/JP2022/017730.
Written Opinion of the International Searching Authority Dated Jul. 5, 2022 in International Application No. PCT/JP2022/017730.
Extended European Search Report dated Aug. 12, 2024 in Application No. 22795586.1.
Breunig, et al., "Software-aided automatic laser optoporation and transfection of cells", Scientific Reports, Jun. 8, 2015, vol. 5, p. 11185, pp. 1-11 (11 pages).
Tosheva, et al., "Between life and death: strategies to reduce phototoxicity in super-resolution microscopy", Journal of Physics D: Applied Physics, Feb. 14, 2020, vol. 53, pp. 1-14 (14 pages).
Office Action issued Apr. 29, 2025 in Australian Patent Application No. 2022263866.

\* cited by examiner

FIG. 3

| FOCAL PLANE | IMAGE OF LIVING CELL | | FOCAL PLANE | IMAGE OF LIVING CELL | |
|---|---|---|---|---|---|
| $P_3$ | $I_3$ | $S_3$ | $P_7$ | $I_7$ | $S_7$ |
| $P_2$ | $I_2$ | $S_2$ | $P_6$ | $I_6$ | $S_6$ |
| $P_1$ | $I_1$ | $S_1$ | $P_5$ | $I_5$ | $S_5$ |
| $P_0$ | $I_0$ | $S_0$ | $P_4$ | $I_4$ | $S_4$ |
| $P_{-1}$ | $L_1$ | $S_{-1}$ | | | |
| $P_{-2}$ | $L_2$ | $S_{-2}$ | | | |

FIG. 4

| FOCAL PLANE | IMAGE OF DEAD CELL | | FOCAL PLANE | IMAGE OF DEAD CELL | |
|---|---|---|---|---|---|
| $P_3$ | $I'_3$ | $S'_3$ | $P_7$ | $I'_7$ | $S'_7$ |
| $P_2$ | $I'_2$ | $S'_2$ | $P_6$ | $I'_6$ | $S'_6$ |
| $P_1$ | $I'_1$ | $S'_1$ | $P_5$ | $I'_5$ | $S'_5$ |
| $P_0$ | $I'_0$ | $S'_0$ | $P_4$ | $I'_4$ | $S'_4$ |
| $P_{-1}$ | $I'_{-1}$ | $S'_{-1}$ | | | |
| $P_{-2}$ | $I'_{-2}$ | $S'_{-2}$ | | | |

CELL LIFE-AND-DEATH DETERMINATION METHOD, CELL LIFE-AND-DEATH DETERMINATION DEVICE, AND CELL LIFE-AND-DEATH DETERMINATION SYSTEM

CROSS-REFERENCE TO RELATED APPLICATION

This application is a continuation application of International Application No., PCT/JP2022/017730 filed Apr. 13, 2022, the disclosure of which is incorporated herein by reference in its entirety. Further, this application claims priority from Japanese Patent Application No. 2021-076026, filed Apr. 28, 2021, the disclosure of which is incorporated herein by reference in their entirety.

BACKGROUND OF THE INVENTION

1. Field of the Invention

The present disclosure relates to a cell life-and-death determination method, a cell life-and-death determination device, and a cell life-and-death determination system.

2. Description of the Related Art

In a cell culture technique, it is necessary to use living cells. Therefore, it is determined whether cells to be used for seeding are alive or dead. A technique related to the determination of whether cells are alive or dead is disclosed, for example, in JP2013-517460A.

SUMMARY OF THE INVENTION

In the related art, techniques related to the determination of whether cells are alive or dead including, for example, the technique disclosed in JP2013-517460A have been studied. However, at present, the techniques are not sufficient.

The present disclosure has been made in view of these circumstances, and an object to be achieved by an embodiment of the present disclosure is to provide a cell life-and-death determination method that uses optical properties of cells.

An object to be achieved by another embodiment of the present disclosure is to provide a cell life-and-death determination device using the cell life-and-death determination method.

An object to be achieved by still another embodiment of the present disclosure is to provide a cell life-and-death determination system including the cell life-and-death determination device.

The present disclosure includes the following aspects.

<1> There is provided a cell life-and-death determination method comprising: acquiring images of a cell captured in a plurality of focal planes including an in-focus plane of the cell in a direction opposite to a side on which the cell is irradiated with light; acquiring an image piece including a central portion and an outer peripheral portion of the cell from each of the images; connecting the image pieces in an order of an imaging direction of the focal plane to create a connected image for analysis; extracting a feature amount from the connected image for analysis; and determining whether the cell is alive or dead on the basis of the feature amount of the connected image for analysis and a predetermined range of the feature amount.

<2> In the cell life-and-death determination method according to <1>, the determining of whether the cell is alive or dead may include determining whether or not the cell is a target cell.

<3> In the cell life-and-death determination method according to <1> or <2>, the determining of whether the cell is alive or dead may be performed by a machine learning device on the basis of a feature amount of a known connected image for reference of the cell and a result of determining whether or not the cell is a living cell.

<4> In the cell life-and-death determination method according to any one of <1> to <3>, the feature amounts of the connected image for analysis may include one or more feature amounts selected from a group consisting of a feature amount related to a lens effect of the cell, a feature amount related to an average refractive index of the cell, a feature amount related to a diameter of the cell, and a feature amount related to a specific gravity of the cell.

<5> In the cell life-and-death determination method according to any one of <1> to <4>, the determining of whether the cell is alive or dead may be performed on a plurality of the cells in a cell suspension.

<6> The cell life-and-death determination method according to <5> may further comprise determining a living cell concentration of the cells in the cell suspension on the basis of a result of determining whether the cells are alive or dead.

<7> The cell life-and-death determination method according to <5> or <6> may further comprise determining a cell survival rate of the cells in the cell suspension on the basis of a result of determining whether the cells are alive or dead.

<8> There is provided a cell life-and-death determination device comprising: an image acquisition unit that acquires images of a cell captured in a plurality of focal planes including an in-focus plane of the cell in a direction opposite to a side on which the cell is irradiated with light; an image piece acquisition unit that acquires an image piece including a central portion and an outer peripheral portion of the cell from each of the images; a connected-image-for-analysis creation unit that connects the image pieces in an order of an imaging direction of the focal plane to create a connected image for analysis; a feature amount extraction unit that extracts a feature amount from the connected image for analysis; and a life-and-death determination unit that determines whether the cell is alive or dead on the basis of the feature amount of the connected image for analysis and a predetermined range of the feature amount.

<9> In the cell life-and-death determination device according to <8>, the life-and-death determination unit may be configured by a machine learning device and may determine whether the cell is alive or dead on the basis of a feature amount of a known connected image for reference of the cell and a result of determining whether or not the cell is a living cell.

<10> The cell life-and-death determination device according to <8> or <9> may further comprise a living cell concentration determination unit that determines a living cell concentration of a plurality of the cells in a cell suspension on the basis of a result of determining whether the cells in the cell suspension are alive or dead.

<11> The cell life-and-death determination device according to <10> may further comprise a cell survival rate determination unit that determines a cell survival rate of the cells in the cell suspension on the basis of the result of determining whether the cells are alive or dead.

<12> There is provided a cell life-and-death determination system comprising: the cell life-and-death determination device according to any one of <8> to <11>; a light source that emits the light; and an imaging device that images the cell; a unit that changes the focal plane.

<13> In the cell life-and-death determination system according to <12>, the unit changing the focal plane may be a stage moving mechanism that moves a stage, on which a holding container holding the cell is placed, to change a distance between the cell and the imaging device.

<14> In the cell life-and-death determination system according to <12>, the unit changing the focal plane may be an imaging device moving mechanism that moves the imaging device to change a distance between the cell and the imaging device.

<15> In the cell life-and-death determination system according to <12>, the imaging device may include a liquid lens as the unit changing the focal plane.

<16> In the cell life-and-death determination device according to any one of <8> to <11>, the cell may be a human synovium-derived mesenchymal stem cell.

<17> There is provided a method for producing a therapeutic agent for arthropathy using the cell life-and-death determination system according to any one of <12> to <15>, in which the cell is a human synovium-derived mesenchymal stem cell.

<18> There is provided a therapeutic agent for arthropathy that is produced by the method for producing a therapeutic agent for arthropathy according to <17>.

An embodiment of the present disclosure provides a cell life-and-death determination method that uses optical properties of cells.

Another embodiment of the present disclosure provides a cell life-and-death determination device using the cell life-and-death determination method.

Still another embodiment of the present disclosure provides a cell life-and-death determination system including the cell life-and-death determination device.

BRIEF DESCRIPTION OF THE DRAWINGS

FIG. 3 is a schematic diagram illustrating an example of an image obtained by imaging a living cell while changing the focal plane.

FIG. 4 is a schematic diagram illustrating an example of an image obtained by imaging a dead cell while changing the focal plane.

DESCRIPTION OF THE PREFERRED EMBODIMENTS

Figure 1:
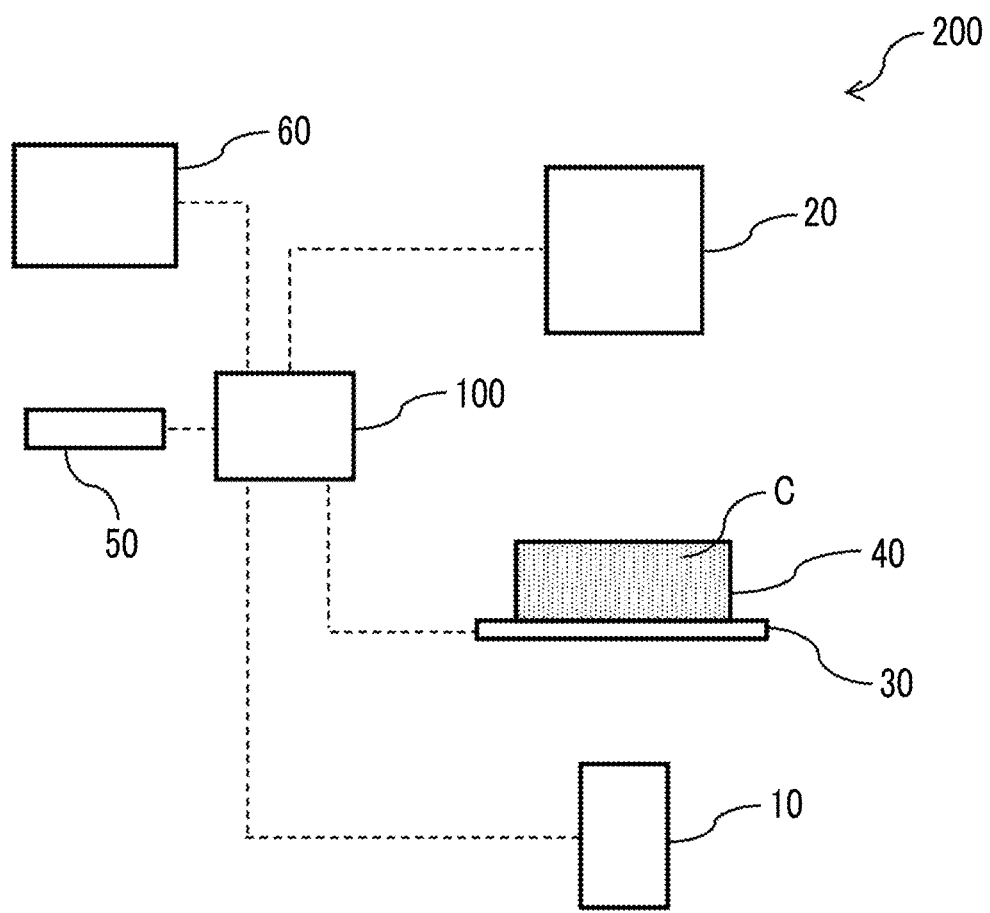
FIG. 1 is a schematic diagram illustrating an example of a cell life-and-death determination system.

Hereinafter, a cell life-and-death determination method and a cell life-and-death determination device according to the present disclosure will be described in detail.

A numerical range described using "to" in the present disclosure means a range that includes numerical values written before and after "to" as a minimum value and a maximum value, respectively.

In the numerical range described stepwise in the present disclosure, an upper limit value or a lower limit value described in a certain numerical range may be replaced with an upper limit value or a lower limit value of another numerical range described stepwise.

Further, in the numerical range described in the present disclosure, an upper limit value or a lower limit value disclosed in a certain range may be replaced with values described in examples.

In the present disclosure, a combination of two or more preferred aspects is a more preferred aspect.

In the present disclosure, in a case in which a plurality of types of substances corresponding to each component are present, the amount of each component means the total amount of the plurality of types of substances, unless otherwise specified.

In the present disclosure, the term "step" includes not only an independent step but also a step of which an intended purpose is achieved even in a case in which the step is not clearly distinguishable from other steps.

The drawings referred to in the following description are exemplarily and schematically illustrated, and the present disclosure is not limited to the drawings. The same reference numerals denote the same components. Further, reference numerals in the drawings may be omitted.

<Cell Life-and-Death Determination Method>

A cell life-and-death determination method according to the present disclosure includes: a step of acquiring images of a cell captured in a plurality of focal planes including an in-focus plane of the cell in a direction opposite to a side on which the cell is irradiated with light (hereinafter, sometimes referred to as an "image acquisition step"); a step of acquiring an image piece including a central portion and an outer peripheral portion of the cell from each of the images (hereinafter, sometimes referred to as an "image piece acquisition step"); a step of connecting the image pieces in an order of an imaging direction of the focal plane to create a connected image for analysis (hereinafter, sometimes referred to as a "connected-image-for-analysis creation step"); a step of extracting a feature amount from the connected image for analysis (hereinafter, sometimes referred to as a "feature amount extraction step"); and a step of determining whether the cell is alive or dead on the basis of the feature amount of the connected image for analysis and a predetermined range of the feature amount (hereinafter, sometimes referred to as a "life-and-death determination step").

For example, JP2013-517460A discloses a cell life-and-death determination method that images a cell in different focal planes and determines whether the cell is alive or dead on the basis of the brightness and darkness of the images. However, the technique disclosed in JP2013-517460A may not be sufficient to determine whether the cell is alive or dead.

In contrast, the cell life-and-death determination method according to the present disclosure creates the connected image from the images of the cell captured in different focal planes, using optical properties of the cell, and analyzes the connected image to determine whether the cell is alive or dead.

Since a living cell is covered with a cell membrane, the living cell has a property of having a spherical shape in a cell suspension (in addition, the spherical shape does not mean a perfect spherical shape). In addition, the living cell has a translucent property. Therefore, the living cell has a property of a spherical lens, and this is called a "lens effect".

Therefore, in a case in which the living cell is irradiated with light, a focusing point (hereinafter, sometimes referred to as a "focusing point of the lens effect") is formed in a direction opposite to a side, on which the living cell is irradiated with light, by the lens effect. In a case in which the living cell is imaged in the direction opposite to the side on which the living cell is irradiated with light, it is possible to acquire an image including the focusing point of the lens effect in the in-focus plane of the living cell.

Therefore, the connected image created from the images of the living cell acquired from a plurality of focal planes including the in-focus plane includes information unique to the living cell.

On the other hand, a dead cell does not have a spherical shape because a cell membrane is broken. In addition, a liquid medium of the cell suspension flows into the dead cell. Therefore, the dead cell does not exhibit the lens effect.

Therefore, even in a case in which the dead cell is irradiated with light, the focusing point of the lens effect is not formed. As a result, even in a case in which the dead cell is imaged in the in-focus plane of the dead cell, it is not possible to acquire an image including the focusing point of the lens effect.

From the above, the connected image created from the living cell is different from the connected image created from the dead cell and has a feature amount unique to the living cell. Therefore, it is possible to determine whether the cell is alive or dead on the basis of the feature amount of the connected image of the cell, whose life or death is unknown, for analysis and a predetermined range of the feature amount.

As described above, in the cell life-and-death determination method according to the present disclosure, whether the cell is alive or read can be appropriately determined in more consideration of information related to whether the cell is alive or read by creating and analyzing the connected image. In addition, in the cell life-and-death determination method according to the present disclosure, since the optical properties of cell are used as described above, it is possible to more easily determine whether the cell is alive or dead without using a staining reagent.

The "predetermined range of the feature amount" means a threshold value for distinguishing whether or not the cell is the living cell. In a case in which the feature amount is within the above-described range, it is possible to determine that the cell is the living cell. A method for determining the "predetermined range of the feature amount" is not particularly limited and may be appropriately determined such that whether the cell is alive or dead can be determined.

In another embodiment, whether the cell is alive or dead may be determined on the basis of the feature amount of a known connected image for reference of the cell and the result of determining whether or not the cell is the living cell. This aspect is preferable in a case in which whether the cell is alive or dead is determined by a machine learning device.

A "target cell" means a specific type of cell to be determined for life or death and may be, for example, a cell used for cell culture or the like.

In some cases, the connected image for analysis and the connected image for reference are simply referred to as a "connected image". In addition, in some cases, the "target cell" is simply referred to as a "cell".

The type of cell is not particularly limited, and it is possible to determine whether various types of living cells are alive or dead. Specifically, the cell may be a mesenchymal stem cell collected or isolated from a biological tissue, and an example of the cell is a human synovium-derived mesenchymal stem cell. Meanwhile, the synovium-derived mesenchymal stem cell is also referred to as a synovium-derived stem cell.

Hereinafter, each step will be described in detail.

Unless otherwise specified, conditions for creating the connected image for analysis (for example, imaging conditions) are the same as the conditions for creating the connected image for reference at least to the extent that it can be determined whether the cell is alive or dead and the cell can be identified. In addition, even in a case in which different connected images for analysis are compared with each other, the conditions for creating these connected images for analysis are the same at least to the extent that the comparison is possible in the determination of whether the cell is alive or dead and the identification of the cell.

[Image Acquisition Step]

In the image acquisition step, the images of the cell captured in a plurality of focal planes including the in-focus plane of the cell in the direction opposite to the side on which the cell is irradiated with light are acquired.

The image of the cell can be acquired by imaging the cell suspension with an imaging device.

A unit for changing the focal plane is not particularly limited, and a method for changing a distance between the cell and the imaging device is given as an example. In addition, an example of a method of performing imaging while keeping the distance between the cell and the imaging device constant is a method for changing the focus of a liquid lens using an imaging device provided with the liquid lens. The focal plane is moved with a change in focal length.

For example, as illustrated in FIG. 1, a holding container 40 in which a cell (cell suspension) C is accommodated may be disposed between a light source 10 and an imaging device 20, and the cell may be imaged while the focal plane is being changed by moving a stage 30 on which the holding container 40 is placed.

In addition, the holding container in which cells (cell suspension) are accommodated may be disposed between the light source and the imaging device, and the cell may be imaged while the focal plane is being changed by moving the imaging device.

Further, the holding container in which cells (cell suspension) are accommodated may be disposed between the light source and the imaging device, and the cell may be imaged while the focal plane is being changed by changing the focus of the liquid lens provided in the imaging device, without moving the imaging device and the stage.

The cell may be imaged while the focal plane is being moved from the light source 10 to the imaging device 20. Alternatively, the cell may be imaged while the focal plane is being changed from the imaging device 20 to the light source 10.

The imaging device consists of a combination of an imaging lens and an area sensor. The imaging lens may be, for example, a telecentric lens or a microscope objective lens.

The type, aperture angle, magnification, and the like of the lens in the imaging device are not particularly limited, but may affect focusing and the divergence of light in the connected image. Therefore, they may be appropriately selected such that imaging can be performed appropriately.

As the magnification of the lens is higher, a visual field is narrower, and the amount of cell suspension that can be imaged per visual field is smaller. Therefore, from the viewpoint of measuring a larger amount of cell suspension, for example, the magnification is preferably about 2 to 4. In addition, as the aperture angle of the lens is narrower, the discrimination sensitivity of the focusing point tends to be higher.

For example, a charge-coupled device (CCD) or a complementary metal-oxide semiconductor (CMOS) can be used as the area sensor of the imaging device. For example, the resolution of the area sensor is preferably set such that one pixel is about 1 μm to 3 μm in consideration of the magnification of the lens.

The light source is not particularly limited, and an example of the light source is a light emitting diode (LED). From the viewpoint of the lens effect, it is preferable that the light source emits parallel light.

The positions of the plurality of focal planes in which the cell is imaged and the number of focal planes are not particularly limited as long as the plurality of focal planes include the in-focus plane of the cell. However, it is preferable to set the positions of the focal planes and the number of focal planes such that focusing and the divergence of light are seen in the connected image.

For example, the cell may be imaged while the focal plane is being moved over a wide range from the lower side to the upper side of the holding container, including from the bottom surface to the top surface of the holding container.

It is preferable that the distance between adjacent focal planes is constant. For example, in a case in which the stage 30 illustrated in FIG. 1 is used, the position of the stage 30 may be specified by an encoder, and the cell may be imaged while the stage 30 is being moved at equal intervals.

It is preferable that the interval at which the focal plane is moved is, for example, about 0.01 mm. In addition, since the moving distance of the focal plane in the cell suspension is shorter than the moving distance of the stage due to the influence of the refractive index of the cell suspension, it is preferable to determine the moving distance of the stage in consideration of this.

For convenience, in a case in which the focal plane is changed, for example, an image may be acquired with a focus on the bottom surface (or the vicinity thereof) of the holding container that holds the cell, and the bottom surface may be used as a reference plane.

In addition, since the connected image is obtained by defining the reference plane and moving the focal plane from the reference plane within a predetermined range, it is possible to create the connected image under the same conditions, which is useful for analyzing the connected image.

A commercially available counting cell, a blood cell counter, or a measurement cell having a structure similar to these can be used as the holding container. A holding container may be used in which a liquid thickness is about 0.1 mm and a cell concentration is about $1\times10^6$ cells/ml in a case in which the cell suspension is accommodated in the holding container and the liquid thickness increases in a case in which the cell concentration is further reduced.

For example, in a case in which the cell suspension includes other substances (for example, other cells, red blood cells, and oil droplets), a substance that has a diameter within a predetermined range and has a shape circularity within a predetermined range may be selected in advance by image processing using image processing software. The effect of shortening the total time required to determine whether the target cell is alive or dead can be obtained by excluding a substance that is clearly different from the target cell.

Figure 2:
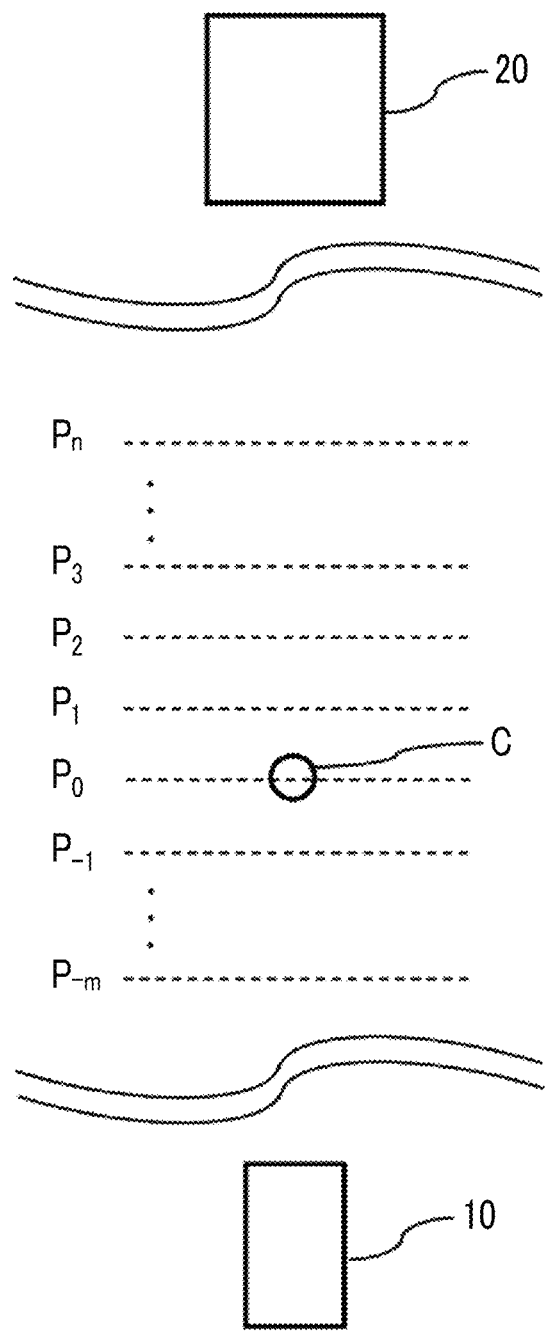
FIG. 2 is a schematic diagram illustrating an example of focal planes.

For example, as illustrated in FIG. 2, a plurality of images may be acquired by irradiating the cell C with light and imaging the cell C in a plurality of focal planes $P_n$ to $P_{-m}$ including an in-focus plane $P_0$ of the cell C in a direction opposite to the side on which the cell C is irradiated with light while changing the focal plane.

The focal plane $P_n$ is an n-th focal plane from the in-focus plane $P_0$ of the cell C in the direction of the imaging device 20. The focal plane $P_{-m}$ is an m-th focal plane from the in-focus plane $P_0$ of the cell C in the direction of the light source 10. At least one of m or n may be an integer equal to or greater than 1, and m+n may be an integer equal to or greater than 1. FIG. 2 illustrates an example in which m is equal to or greater than 2 and n is equal to or greater than 4.

Hereinafter, an example of a case in which the cell C is the living cell will be described.

In a case in which the cell C is the living cell, for example, images $I_7$ to $I_{-2}$ of the living cell are obtained by imaging the living cell in a plurality of focal planes $P_7$ to $P_{-2}$ including the in-focus plane $P_0$ of the living cell while changing the focal plane as illustrated in FIG. 3.

The image $I_0$ is captured in the in-focus plane $P_0$ of the living cell, and the contour of the living cell is clear. Further, the focusing point of the lens effect whose contour is unclear is present in the central portion of the living cell.

The image $I_1$ is captured in the first focal plane $P_1$ from the in-focus plane $P_0$ of the living cell in the direction of the imaging device 20, and the contour of the living cell is unclear. In addition, the focusing point of the lens effect is present in the central portion of the living cell, and the contour of the focusing point is clear. That is, the focal plane $P_1$ is an example of the in-focus plane of the focusing point of the lens effect.

The image $I_2$ and the image $I_3$ are captured in the second focal plane $P_2$ and the third focal plane $P_3$ from the in-focus plane $P_0$ of the living cell in the direction of the imaging device 20, respectively, and the contour of the living cell is unclear. Further, the focusing point of the lens effect whose contour is unclear is present in the central portion of the living cell.

The images $I_4$ to $I_7$ are captured in the fourth to seventh focal planes $P_4$ to $P_7$ from the in-focus plane $P_0$ of the living cell in the direction of the imaging device 20, respectively, and the contour of the living cell is unclear. In addition, the focusing point of the lens effect is not seen.

The image $I_{-1}$ is captured in the first focal plane $P_{-1}$ from the in-focus plane $P_0$ of the living cell in the direction of the light source 10, and the contour of the living cell is unclear. Further, the focusing point of the lens effect whose contour is unclear is present in the central portion of the living cell.

The image $I_{-2}$ is captured in the second focal plane $P_{-2}$ from the in-focus plane $P_0$ of the living cell in the direction of the light source 10, and the contour of the living cell is unclear. In addition, the focusing point of the lens effect is not seen.

As illustrated in, for example, the images $I_7$ to $I_{-2}$, the contour of the living cell tends to be larger as the focal plane is farther from the in-focus plane $P_0$ of the living cell.

On the side (that is, the side of the imaging device 20) on which the focusing point of the lens effect is formed, the size of the focusing point of the lens effect tends to be larger as the focal plane is farther from the in-focus plane $P_1$ of the focusing point of the lens effect, for example, as shown in the image $I_1$ and the image $I_2$. However, in the focal plane $P_3$ that is far from the in-focus plane $P_1$ of the focusing point of the lens effect, the size of the focusing point of the lens effect is small as shown in the image $I_3$. In the focal plane $P_4$ that is further from the in-focus plane $P_1$, the focusing point is not seen.

In addition, on a side (that is, the side of the light source 10) opposite to the side on which the focusing point of the lens effect is formed, the size of the focusing point of the lens effect tends to be smaller as the focal plane is farther from the in-focus plane $P_1$ of the focusing point of the lens effect, for example, as shown in the image $I_{-1}$. Further, in the focal plane $P_{-2}$ that is further from the in-focus plane $P_1$, the focusing point of the lens effect is not seen.

Next, an example of a case in which the cell is the dead cell will be described.

In a case in which the cell is the dead cell, for example, images $I'_7$ to $I'_{-2}$ of the dead cell are obtained by imaging the dead cell in a plurality of focal planes $P_7$ to $P_{-2}$ including an in-focus plane $P_0$ of the dead cell while changing the focal plane as illustrated in FIG. 4.

The image $I'_0$ is captured in the in-focus plane $P_0$ of the dead cell, and the contour of the dead cell is clear.

The image $I'_1$, is captured in the first focal plane $P_1$ from the in-focus plane $P_0$ of the dead cell in the direction of the imaging device 20, and the contour of the dead cell is unclear.

The image $I'_2$ is captured in the second focal plane $P_2$ from the in-focus plane $P_0$ of the dead cell in the direction of the imaging device 20, and the contour of the dead cell is unclear. In addition, the dead cell is opaque as compared to the living cell because the cell membrane is broken and light is scattered on the outer peripheral surface of the dead cell. As a result, in a case in which the dead cell is irradiated with light, a phenomenon similar to the diffraction of plane waves of light caused by a shielding material occurs, and a bright portion is formed in the vicinity of the center of the dead cell in the direction opposite to the side on which the dead cell is irradiated with light. This is a result of overlapping diffracted light components (hereinafter, the above-described portion is referred to as a "focusing point of diffracted light"). The focusing point of the diffracted light is present in the central portion of the dead cell in the image $I'_2$, and the contour of the focusing point is clear. That is, the focal plane $P_2$ is an example of the in-focus plane of the focusing point of the diffracted light.

The images $I'_3$ to $I'_7$ are captured in the third to seventh focal planes $P_3$ to $P_7$ from the in-focus plane $P_0$ of the dead cell in the direction of the imaging device 20, respectively, and the contour of the dead cell is unclear. In addition, the focusing point of the diffracted light whose contour is unclear is present in the central portion of the dead cell.

The images $I'_{-1}$ and $I'_{-2}$ are captured in the first and second focal planes $P_{-1}$ and $P_{-2}$ from the in-focus plane $P_0$ of the dead cell in the direction of the light source 10, respectively, and the contour of the dead cell is unclear.

Similarly to the living cell, the contour of the dead cell tends to be larger as the focal plane is farther from the in-focus plane $P_0$ of the dead cell, for example, as shown in the images $I_7$ to $I_{-2}$.

The size of the focusing point of the diffracted light tends to be larger as the focal plane is further from the in-focus plane $P_2$ of the focusing point of the diffracted light, for example, as shown in the images $I_7$ to $I_{-2}$.

The above is an example described with reference to FIGS. 3 and 4, and the contour of the cell and the appearance of the focusing point may differ depending on, for example, the sphericity and size of the cell.

In some cases, the focusing point of the lens effect and the focusing point of the diffracted light are simply referred to as a "focusing point".

[Image Piece Acquisition Step]

In the image piece acquisition step, an image piece including the central portion and the outer peripheral portion of the cell is acquired from each of the images obtained in the image acquisition step.

The image piece acquisition step may be performed by, for example, image processing using image processing software.

The position where the image piece is acquired from the image of the cell is not particularly limited as long as the image piece includes the central portion and the outer peripheral portion of the cell.

It is preferable that the image piece includes a portion in which the length of the cell has the maximum value (that is, a portion in which the length of a straight line connecting any two points on the contour of the cell has the maximum value).

For example, as illustrated in FIG. 3, image pieces $S_7$ to $S_{-2}$ including the portion in which the length of the living cell has the maximum value may be acquired, or image pieces $S'_7$ to $S'_{-2}$ including the portion in which the length of the dead cell has the maximum value may be acquired.

In addition, preprocessing may be performed on each image before the image piece is acquired from each image of the cell. An example of the preprocessing is a process that sets concentric circles, which have the central portion of the cell as their centers and have different radii, in units of pixels, calculates an average value of brightness on the circumference of each concentric circle, and draws a concentric circle whose brightness on the circumference has the average value (that is, a concentric circle whose brightness on the circumference is averaged and which has the same radius as the original concentric circle) to reconstruct the image of the cell. This makes it possible to obtain symmetrical images that have the central portion of the cell as their centers. Therefore, in a case in which the image piece is acquired, it is possible to remove the influence of a direction in which the image piece is cut out.

Figure 5:
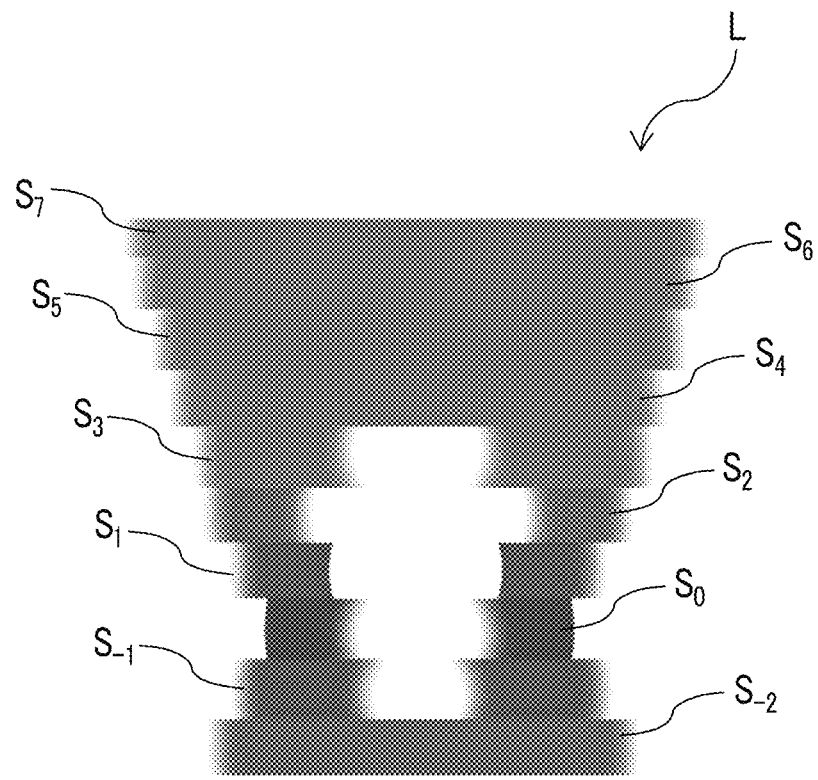
FIG. 5 is a schematic diagram illustrating an example of a connected image obtained from the living cell.
Figure 6:
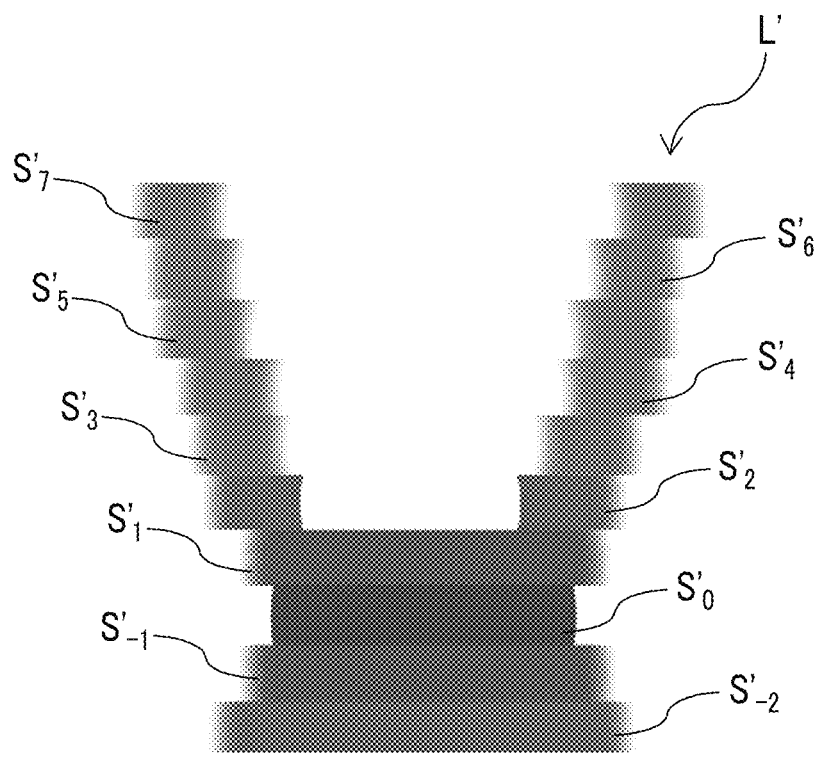
FIG. 6 is a schematic diagram illustrating an example of a connected image obtained from the dead cell.

The use of the image piece acquired from the image subjected to the preprocessing makes it possible to obtain symmetric connected images (for example, the bilaterally symmetric connected images illustrated in FIGS. 5 and 6) and makes it easier to extract the feature amount from the connected image in the subsequent feature amount extraction step.

[Connected-Image-for-Analysis Creation Step]

In the connected-image-for-analysis creation step, each image piece obtained in the image piece acquisition step is connected in the order of the imaging direction of the focal plane to create a connected image for analysis.

The connected-image-for-analysis creation step may be performed by, for example, image processing using image processing software.

A method for connecting the image pieces is not particularly limited as long as the image pieces are connected in the order of the imaging direction of the focal plane. It is preferable to connect the image pieces along a straight line connecting the central portions of the cell in each image piece such that the long sides of the image pieces are in contact with each other.

For example, as illustrated in FIG. 5, the image pieces $S_7$ to $S_{-2}$ of the living cell acquired from FIG. 3 are connected in the order of the imaging direction of the focal plane along a line connecting the central portions of the living cell in each image piece to obtain a connected image L for analysis of the living cell.

In addition, for example, as illustrated in FIG. 6, the image pieces $S'_7$ to $S'_{-2}$ of the dead cell acquired from FIG. 4 are connected in the order of the imaging direction of the focal plane along a line connecting the central portions of the dead cell in each image piece to obtain a connected image L' for analysis of the dead cell.

[Feature Amount Extraction Step]

In the feature amount extraction step, the feature amount is extracted from the connected image for analysis obtained in the connected-image-for-analysis creation step.

The feature amount extraction step may be performed by, for example, image processing using image processing software.

(Feature Amount Extracted from Connected Image)

The connected image includes various types of information related to the cell. For example, the following feature amounts 1 to 11 can be obtained.

—Feature Amount 1— (Determination of Whether Cell is Alive or Dead Based on Whether Focusing Point of Lens Effect is Present or Absent)

The connected image includes information related to whether the cell is alive or dead based on whether the focusing point of the lens effect is present or absent.

The connected image includes the image piece of the in-focus plane of the cell. In the in-focus plane of the cell, the living cell has the focusing point of the lens effect, but the dead cell does not have the focusing point of the lens effect.

For example, the connected image L of the living cell illustrated in FIG. 5 has the focusing point of the lens effect in the image piece $S_0$ of the in-focus plane $P_0$ of the living cell. On the other hand, for example, the connected image L' of the dead cell illustrated in FIG. 6 does not have the focusing point of the lens effect in the image piece $S'_0$ of the in-focus plane $P_0$ of the dead cell.

Therefore, it is possible to determine whether the cell is alive or dead on the basis of whether the focusing point of the lens effect is present or absent.

For example, the brightness of a central portion of the image piece of the in-focus plane of the cell may be set as the feature amount 1, and whether the cell is alive or dead may be determined on the basis of a predetermined range of the feature amount 1. Therefore, for the connected image for analysis, in a case in which the feature amount 1 is within the above-described range, it is possible to determine that the cell is the living cell.

In addition, in another embodiment, whether the cell is alive or dead may be determined on the basis of the feature amount 1 of the connected image for analysis, the feature amount 1 of the known connected image for reference of the cell, and the result of determining whether or not the cell is the living cell.

—Feature Amount 2— (Determination of Whether Cell is Alive or Dead Based on Start Position of Focusing Point)

The connected image includes information related to whether the cell is alive or dead based on the start position of the focusing point.

The "start position of the focusing point" means the in-focus plane of the focusing point of the lens effect or the diffracted light.

The "start position of the focusing point" in the connected image means the image piece of the in-focus plane of the focusing point of the lens effect or the diffracted light.

In the living cell, the start position of the focusing point of the lens effect reflects the average refractive index of the cell.

In the case of the living cell, for example, as illustrated in FIG. 3, the in-focus plane $P_1$ of the focusing point of the lens effect is the start position of the focusing point of the lens effect.

On the other hand, in the case of the dead cell, for example, as illustrated in FIG. 4, the in-focus plane $P_2$ of the focusing point of the diffracted light is the start position of the focusing point of the diffracted light.

For example, as illustrated in FIGS. 3 and 4, the start position of the focusing point of the lens effect is closer to the cell than the start position of the focusing point of the diffracted light. The reason is that, while the focusing point of the lens effect is formed by the focusing of the light transmitted through the living cell in the vicinity of the living cell, the focusing point of the diffracted light is formed by the focusing of the light passing through the vicinity of the outer peripheral surface of the dead cell at the position that is relatively far from the dead cell. That is, the focusing point of the lens effect formed in the living cell is formed closer to the cell than the focusing point of the diffracted light formed in the dead cell.

For example, in the connected image L of the living cell illustrated in FIG. 5, the image piece $S_1$ of the start position (in-focus plane $P_1$) of the focusing point of the lens effect is adjacent to the image piece $S_0$ of the in-focus plane $P_0$ of the living cell, and the start position of the focusing point of the lens effect is close to the in-focus plane $P_0$ of the living cell.

On the other hand, for example, in the connected image L' of the dead cell illustrated in FIG. 6, the image piece $S'_2$ of the start position (in-focus plane $P_2$) of the focusing point of the diffracted light is not adjacent to the image piece $S'_0$ of the in-focus plane $P_0$ of the dead cell, and the start position of the focusing point of the diffracted light is far from the in-focus plane $P_0$ of the dead cell.

Therefore, it is possible to determine whether the cell is alive or dead on the basis of the start position of the focusing point.

For example, the start position of the focusing point may be specified by the distance from the in-focus plane of the cell, and the feature amount 2 may be set. For example, the length between the image piece of the in-focus plane of the cell and the image piece of the start position of the focusing point (that is, the in-focus plane of the focusing point) in the direction in which the image pieces are connected may be set as the feature amount 2, and whether the cell is alive or dead may be determined on the basis of a predetermined range of the feature amount 2. Therefore, for the connected image for analysis, in a case in which the feature amount 2 is within the above-described range, it is possible to determine that the cell is the living cell.

In addition, in another embodiment, whether the cell is alive or dead may be determined on the basis of the feature amount 2 of the connected image for analysis, the feature amount 2 of the known connected image for reference of the cell, and the result of determining whether or not the cell is the living cell.

—Feature Amount 3— (Determination of Whether Cell is Alive or Dead Based on Continuous Length of Focusing Point)

The connected image includes information related to whether the cell is alive or dead based on the continuous length of the focusing point.

The "continuous length of the focusing point" means a distance from the start position of the focusing point of the lens effect or the diffracted light to the focal plane in which the focusing point disappears.

In the connected image, the "continuous length of the focusing point" means the shortest length from the image piece of the in-focus plane of the focusing point of the lens effect or the diffracted light to the image piece of the focal plane in which the focusing point disappears.

In the living cell, the continuous length of the focusing point of the lens effect reflects the average refractive index of the cell.

In the case of the living cell, for example, as illustrated in FIG. 3, the distance from the start position (in-focus plane $P_1$) of the focusing point of the lens effect to the focal plane $P_4$ in which the focusing point of the lens effect disappears is the continuous length of the focusing point of the lens effect.

On the other hand, in the case of the dead cell, for example, as illustrated in FIG. 4, the distance from the start position (in-focus plane $P_2$) of the focusing point of the diffracted light to the focal plane in which the focusing point of the diffracted light disappears is the "continuous length of the focusing point" of the diffracted light. The focusing point continues up to the focal plane that is further away from the in-focus plane $P_0$ than the focal plane $P_4$, which is not illustrated in FIG. 4.

At the focusing point of the lens effect, light transmitted through a portion closer to the center of the living cell is focused at a position that is farther from the living cell, and light transmitted through a portion farther from the center of the living cell is focused at a position that is closer to the living cell. As a result, since the focusing points are connected according to a portion of the living cell through which light is transmitted, the focusing point of the lens effect has the continuous length of the focusing point. In addition, for the focusing point of the lens effect, the intensity of light decreases in a short distance due to divergence. Furthermore, in a case in which the living cell is irradiated with white light, a blue component (short-wavelength component) is focused at a position closer to the cell than a red component (long-wavelength component). Therefore, a difference in wavelength also contributes to the continuous length of the focusing point of the lens effect.

On the other hand, the focusing point of the diffracted light is formed by the focusing of light passing through the vicinity of the outer peripheral surface of the dead cell, and a change of an interference pattern depending on the distance from the dead cell extends over a relatively long distance. Therefore, the focusing point of the diffracted light has a longer continuous length than that of the lens effect. That is, the focusing point of the living cell has a shorter continuous length than the focusing point of the dead cell.

For example, in the connected image L of the living cell illustrated in FIG. 5, the focusing point of the lens effect is continuous from the image piece $S_1$ to the image piece $S_3$.

On the other hand, for example, in the connected image L' of the dead cell illustrated in FIG. 6, the focusing point of the diffracted light is continuous from the image piece S'2 to the image piece S'7.

As illustrated in FIGS. 5 and 6, the continuous length of the focusing point in the connected image L of the living cell is shorter than the continuous length of the focusing point in the connected image L' of the dead cell.

Therefore, it is possible to determine whether the cell is alive or dead on the basis of the continuous length of the focusing point.

For example, in a region in which the focusing point is continuous, a length along a direction in which the image pieces are connected may be set as the feature amount 3, and whether the cell is alive or dead may be determined on the basis of a predetermined range of the feature amount 3. Therefore, for the connected image for analysis, in a case in which the feature amount 3 is within the above-described range, it is possible to determine that the cell is the living cell.

In addition, in another embodiment, whether the cell is alive or dead may be determined on the basis of the feature amount 3 of the connected image for analysis, the feature amount 3 of the known connected image for reference of the cell, and the result of determining whether or not the cell is the living cell.

—Feature Amount 4— (Identification of Cell Based on Start Position of Focusing Point)

The connected image includes information related to the identification of the cell based on the start position of the focusing point.

In the living cell, the start position of the focusing point of the lens effect reflects the average refractive index of the cell. For other substances (for example, other cells, red blood cells, and oil droplets) having an average refractive index different from that of the target cell, the start position of the focusing point is different from that of the target cell.

Therefore, it is possible to determine whether or not the cell to be determined for life or death is the target cell on the basis of the start position of the focusing point.

For example, the start position of the focusing point may be specified by the distance from the in-focus plane of the cell, and the feature amount 4 may be set. For example, the length between the image piece of the in-focus plane of the cell and the image piece of the start position of the focusing point (that is, the in-focus plane of the focusing point) in the direction in which the image pieces are connected may be set as the feature amount 4, and whether the cell is alive or dead may be determined on the basis of a predetermined range of the feature amount 4. Therefore, for the connected image for analysis, in a case in which the feature amount 4 is within the above-described range, it is possible to determine that the cell to be determined for life or death is the target cell.

In addition, in another embodiment, whether the cell is alive or dead may be determined on the basis of the feature amount 4 of the connected image for analysis, the feature amount 4 of the known connected image for reference of the cell, and the result of determining whether or not the cell is the living cell.

The feature amount 4 may be the same as the feature amount 2. In addition, the feature amount 4 may be different from the feature amount 2. For example, the feature amount 4 may be set to be more appropriate for identifying the cell, and the feature amount 2 may be set to be more appropriate for determining whether the cell is alive or dead.

—Feature Amount 5— (Identification of Cell Based on Continuous Length of Focusing Point)

The connected image includes information related to the identification of the cell based on the continuous length of the focusing point.

In the living cell, the continuous length of the focusing point of the lens effect reflects the average refractive index of the cell. Therefore, for other substances (for example, other cells, red blood cells, and oil droplets) having an average refractive index different from that of the target cell, the continuous length of the focusing point is different from that of the target cell.

Therefore, it is possible to determine whether or not the cell to be determined for life or death is the target cell on the basis of the continuous length of the focusing point.

For example, in a region in which the focusing point is continuous, a length along the direction in which the image pieces are connected may be set as the feature amount 5, and whether the cell is alive or dead may be determined on the basis of a predetermined range of the feature amount 5. Therefore, for the connected image for analysis, in the case in which the feature amount 5 is within the above-described range, it is possible to determine that the cell to be determined for life or death is the target cell.

In addition, in another embodiment, whether the cell is alive or dead may be determined on the basis of the feature amount 5 of the connected image for analysis, the feature amount 5 of the known connected image for reference of the cell, and the result of determining whether or not the cell is the living cell.

The feature amount 5 may be the same as the feature amount 3. In addition, the feature amount 5 may be different from the feature amount 3. For example, the feature amount 5 may be set to be more appropriate for identifying the cell, and the feature amount 3 may be set to be more appropriate for determining whether the cell is alive or dead.

For the feature amount 4 and the feature amount 5, for example, unlike the living cell, the red blood cell has a shape like a concave lens. Therefore, in a case in which the red blood cell is irradiated with light, a focusing point is formed on a side opposite to the side on which the red blood cell is irradiated with light. In addition, a focusing point is also formed on the side on which the red blood cell is irradiated with light. In addition to the difference in the appearance of the focusing point, the red blood cell may differ from the living cell in the start position of the focusing point and the continuous length of the focusing point.

—Feature Amount 6— (Identification of Cell Based on Size of Cell in In-Focus Plane)

The connected image may include information related to the identification of the cell based on the size of the cell in the in-focus plane.

The connected image includes the image piece of the in-focus plane of the cell. Therefore, in a case in which the image piece of the in-focus plane of the cell includes a portion in which the length of the cell has the maximum value (that is, a portion in which the length of a straight line connecting any two points on the contour of the cell has the maximum value), the maximum length of the portion can be used as the diameter of the cell. Then, for example, it is examined whether or not the diameter of the cell to be determined for life or death is the same as the known diameter of the target cell. In a case in which the diameters are not the same, it is possible to determine that the cell to be determined for life or death is not the target cell.

Therefore, it is possible to determine whether or not the cell to be determined for life or death is the target cell on the basis of the size of the cell in the in-focus plane.

For example, for the image piece of the in-focus plane of the cell to be determined for life or death, the length of a portion in which the length of the cell has the maximum value (that is, a portion in which the length of a straight line connecting any two points on the contour of the cell has the maximum value) may be set as the feature amount 6, and whether the cell is alive or dead may be determined on the basis of a predetermined range of the feature amount 6. Therefore, for the connected image for analysis, in the case in which the feature amount 6 is within the above-described range, it is possible to determine that the cell to be determined for life or death is the target cell.

In addition, in another embodiment, whether the cell is alive or dead may be determined on the basis of the feature amount 6 of the connected image for analysis, the feature amount 6 of the known connected image for reference of the cell, and the result of determining whether or not the cell is the living cell.

—Feature Amount 7— (Identification of Cell Based on Position of In-Focus Plane)

The connected image includes information related to the identification of the cell based on the position of the in-focus plane.

For example, in a cell suspension including the target cell and other substances (for example, other cells, red blood cells, and oil droplets), in a case in which the specific gravity of the cell is different from the specific gravity of other substances, there is a difference in how the cell and other substances sink (the degree of sinking) in the cell suspension, and the position of the cell is different from the positions of other substances in the depth direction of the cell suspension. Therefore, in a case in which the cell and other substance are imaged in the same focal plane to create a connected image, the position of the image piece of the in-focus plane of the cell is different from the positions of the image pieces of the in-focus planes of other substances (for example, the height in the direction in which the image pieces are connected). Then, for example, it is examined whether or not the position of the image piece of the in-focus plane of the cell to be determined for life or death is the same as the position of the image piece of the known in-focus plane of the target cell. In a case in which the positions are not the same, it is possible to determine that the cell to be determined for life or death is not the target cell.

Therefore, it is possible to determine whether or not the cell to be determined for life or death is the target cell on the basis of the position of the in-focus plane.

For example, a length between the image piece of the in-focus plane of the cell to be determined for life or death and the image piece of the lowermost focal plane in the direction in which the image pieces are connected may be set as the feature amount 7, and whether the cell is alive or dead may be determined on the basis of a predetermined range of the feature amount 7. Therefore, for the connected image for analysis, in the case in which the feature amount 7 is within the above-described range, it is possible to determine that the cell to be determined for life or death is the target cell.

In addition, in another embodiment, whether the cell is alive or dead may be determined on the basis of the feature amount 7 of the connected image for analysis, the feature amount 7 of the known connected image for reference of the cell, and the result of determining whether or not the cell is the living cell.

—Feature Amount 8— (Identification of Cell Based on Connected Shape of Focusing Points)

The connected image includes information related to the identification of the cell based on the connected shape of the focusing points.

The "connected shape of the focusing points" means the shape of a portion formed by connecting the focusing points in the connected image.

For example, for the connected image for analysis, an image of a portion in which the focusing points are connected may be set as the feature amount 8, and whether or not the cell to be determined for life or death is the target cell may be determined by the machine learning device on the basis of the feature amount 8 of the connected image for analysis, the feature amount 8 of the known connected image for reference of the cell, and the result of determining whether or not the cell is the living cell.

The connected shape of the focusing points is related to the size of the focusing point in addition to the start position of the focusing point and the continuous length of the focusing point and reflects the average refractive index of the cell in the living cell. Therefore, other substances (for example, other cells, red blood cells, and oil droplets) having an average refractive index different from that of the target cell are different from the target cell in the connected shape of the focusing points.

Therefore, it is possible to determine whether or not the cell to be determined for life or death is the target cell on the basis of the connected shape of the focusing points.

—Feature Amount 9— (Identification of Cell Based on Color Distribution of Focusing Point)

The connected image may include information related to the identification of the cell based on a color distribution of the focusing point.

In a case in which the living cell is irradiated with white light, a blue component (short-wavelength component) is focused at a position closer to the cell than a red component (long-wavelength component). A color distribution is seen at the focusing point of the lens effect. The color distribution of the focusing point of the lens effect reflects the average refractive index of the cell. Therefore, other substances (for example, other cells, red blood cells, and oil droplets) having an average refractive index different from that of the target cell are different from the target cell in the color distribution of the focusing point.

Therefore, it is possible to determine whether or not the cell to be determined for life or death is the target cell on the basis of the color distribution of the focusing point.

For example, in the case of the living cell, the color separation of the focusing point of the lens effect is seen, and a color distribution is seen in which the vicinity of the cell is colored blue and a relatively far portion is colored red. On the other hand, for example, in the case of the red blood cell, the color separation of the focusing point is weak due to a shape like a concave lens, and the focusing point tends to appear relatively white.

For example, for the connected image for analysis, an image of a portion in which the focusing points are connected may be set as the feature amount 9, and whether or not the cell to be determined for life or death is the target cell may be determined by the machine learning device on the basis of the feature amount 9 of the connected image for analysis, the feature amount 9 of the known connected image for reference of the cell, and the result of determining whether or not the cell is the living cell.

—Feature Amount 10— (Determination of Whether Cell is Alive or Dead and Identification of Cell Based on Rate of Match Between Connected Images)

As described above, the connected image includes information related to the determination of whether the cell is alive or dead and the identification of the cell. Therefore, it is possible to determine whether the cell is alive or dead and whether or not the cell to be determined for life or death is the target cell, on the basis of the rate of match between the connected image for analysis and the connected image for reference.

Therefore, the connected image for analysis may be set as the feature amount 10, and whether or not the cell to be determined for life or death is the living cell and whether or not the cell is the target cell may be determined by the machine learning device on the basis of the feature amount 10 of the connected image for analysis, the feature amount 10 of the known connected image for reference of the cell, and the result of determining whether or not the cell is the living cell.

—Feature Amount 11— (Determination of Whether Cell is Alive or Dead Based on Transmission Amount of Lens Effect of Cell)

The connected image includes information related to whether the cell is alive or dead based on the transmission amount of the lens effect of the cell.

The "transmission amount of the lens effect" of the cell means the transmission amount of light through the cell in a case in which the cell has the lens effect.

In the connected image, the "transmission amount of the lens effect" of the cell means a weighted sum of the average brightness of "a plurality of image pieces in the imaging direction" starting from the image piece of the in-focus plane of the cell and the average brightness of "a plurality of image pieces in the direction of the light source" starting from the image piece of the in-focus plane of the cell in a case in which the cell has the lens effect. A weighting coefficient is not particularly limited and may be set as appropriate.

In some cases, the dead cell immediately after the cell membrane is broken has the focusing point caused by the lens effect as an intermediate state, similarly to the living cell. In the dead cell, light is scattered on the outer peripheral surface due to the broken cell membrane. Therefore, the transmission amount of the lens effect is less than that in the living cell. Therefore, it is possible to determine whether the cell is alive or dead on the basis of the transmission amount of the lens effect. It is assumed that the output of the light source is managed to be constant.

The average brightness of the image pieces in the imaging direction with respect to the in-focus plane of the cell is, for example, the average brightness of the image piece $S_0$ of the in-focus plane $P_0$ to the image piece Sn of the focal plane $P_n$ illustrated in FIG. 2.

The average brightness of the image pieces in the direction of the light source with respect to the in-focus plane of the cell is, for example, the average brightness of the image piece $S_0$ of the in-focus plane $P_0$ to the image piece $S_{-m}$ of the focal plane $P_{-m}$ illustrated in FIG. 2 (for example, n=m is desirable).

The weighted sum of the average brightness of "a plurality of image pieces in the imaging direction" starting from the image piece of the in-focus plane of the cell and the average brightness of "a plurality of image pieces in the direction of the light source" starting from the in-focus plane of the cell may be set as the feature amount 11, and whether the cell is alive or dead may be determined on the basis of a predetermined range of the feature amount 11.

In the case of a multi-wavelength light source (for example, a white LED) and a spectral imaging device (for example, an RGB color camera), a connected image may be created for each color, and the average brightness of "the plurality of image pieces in the imaging direction" and the average brightness of "the plurality of image pieces in the direction of the light source" may be combined from different colors to determine whether the cell is alive or dead.

The feature amounts 1 to 11 described above are examples of the feature amounts obtained from the connected images, and the determination of whether the cell is alive or dead and the identification of the cell may be performed on the basis of other feature amounts.

The feature amount 1 and the feature amount 11 are related to the lens effect of the cell. In addition, the feature amounts 2 to 5 are related to the average refractive index of the cell. Further, the feature amount 6 is related to the diameter of the cell. Furthermore, the feature amount 7 is related to the specific gravity of the cell. Moreover, the feature amount 8 and the feature amount 9 are related to the form of the connected image. Further, the feature amount 10 is related to all of the average refractive index of the cell, the diameter of the cell, and the specific gravity of the cell.

As described above, since many feature amounts can be obtained from the connected image, the connected image is effective not only for determining whether the cell is alive or dead but also for identifying the cell.

It is preferable that the feature amounts used for determining whether the cell is alive or dead include one or more feature amounts selected from the group consisting of the feature amounts 1 to 11, that is, one or more feature amounts selected from the group consisting of the feature amount related to the lens effect of the cell, the feature amount related to the average refractive index of the cell, the feature amount related to the diameter of the cell, and the feature amount related to the specific gravity of the cell.

[Life-and-Death Determination Step]

In the life-and-death determination step, it is determined whether the cell is alive or dead on the basis of the feature amount of the connected image for analysis and a predetermined range of the feature amount. In another embodiment, whether the cell is alive or dead may be determined on the basis of the feature amount of the known connected image for reference of the cell and the result of determining whether or not the cell is the living cell.

In addition to the determination of whether the cell is alive or dead, the determination of whether or not the cell to be determined for life or death is the target cell can be performed on the basis of a predetermined range of the feature amount.

Further, in a case in which, in addition to the determination of whether the cell is alive or dead, the determination of whether or not the cell to be determined for life or death is the target cell is performed, whether the cell is alive or dead may be determined on the basis of the feature amount of the known connected image for reference of the target cell and the result of determining whether or not the cell is the living cell.

The determination of whether the cell is alive or dead can include the determination of whether or not the cell to be determined for life or death is the target cell, that is, the identification of the cell.

An example of this aspect is a case in which whether the cell is alive or dead is determined using the feature amount 2 (or the feature amount 4) based on the start position of the focusing point. The feature amount 2 can also function the feature amount 4 (or the feature amount 2) based on the start position of the focusing point to determine whether or not the cell to be determined for life or death is the target cell.

In addition, another example of this aspect is a case in which whether the cell is alive or dead is determined using the feature amount 3 (or the feature amount 4) based on the continuous length of the focusing point. The feature amount 3 can also function as the feature amount 4 (or the feature amount 3) based on the continuous length of the focusing point to determine whether or not the cell to be determined for life or death is the target cell.

Further, still another example of this aspect is a case in which the feature amount 10 based on the ratio of match between the connected images is used. The determination of whether the cell is alive or dead and the determination of whether or not the cell to be determined for life or death is the target cell are performed at the same time.

Whether the cell is alive or dead may be determined using any one of the feature amount 1, the feature amount 2, the feature amount 3, or the feature amount 11. In addition, from the viewpoint of further improving the accuracy of the determination of whether the cell is alive or dead, whether the cell is alive or dead may be determined using a combination of two or more of the feature amounts 1 to 3 and the feature amount 11.

The identification of the cell (that is, the determination of whether or not the cell to be determined for life or death is the target cell) may be performed using any one of the feature amounts 4 to 9. From the viewpoint of further improving the accuracy of the identification of the cell, the identification of the cell may be performed using a combination of two or more of the feature amounts 4 to 9.

In addition, the determination of whether the cell is alive or dead and the identification of the cell may be performed at the same time using the feature amount 10.

(Machine Learning Device)

The determination of whether the cell is alive or dead (in some aspects, it may include the identification of the cell) may be performed using the machine learning device. The machine learning device may be constructed by any one of a neural network, a support vector machine, or a boosting method. It is preferable that the machine learning device is constructed by the neural network and subjected to deep learning.

Figure 7:
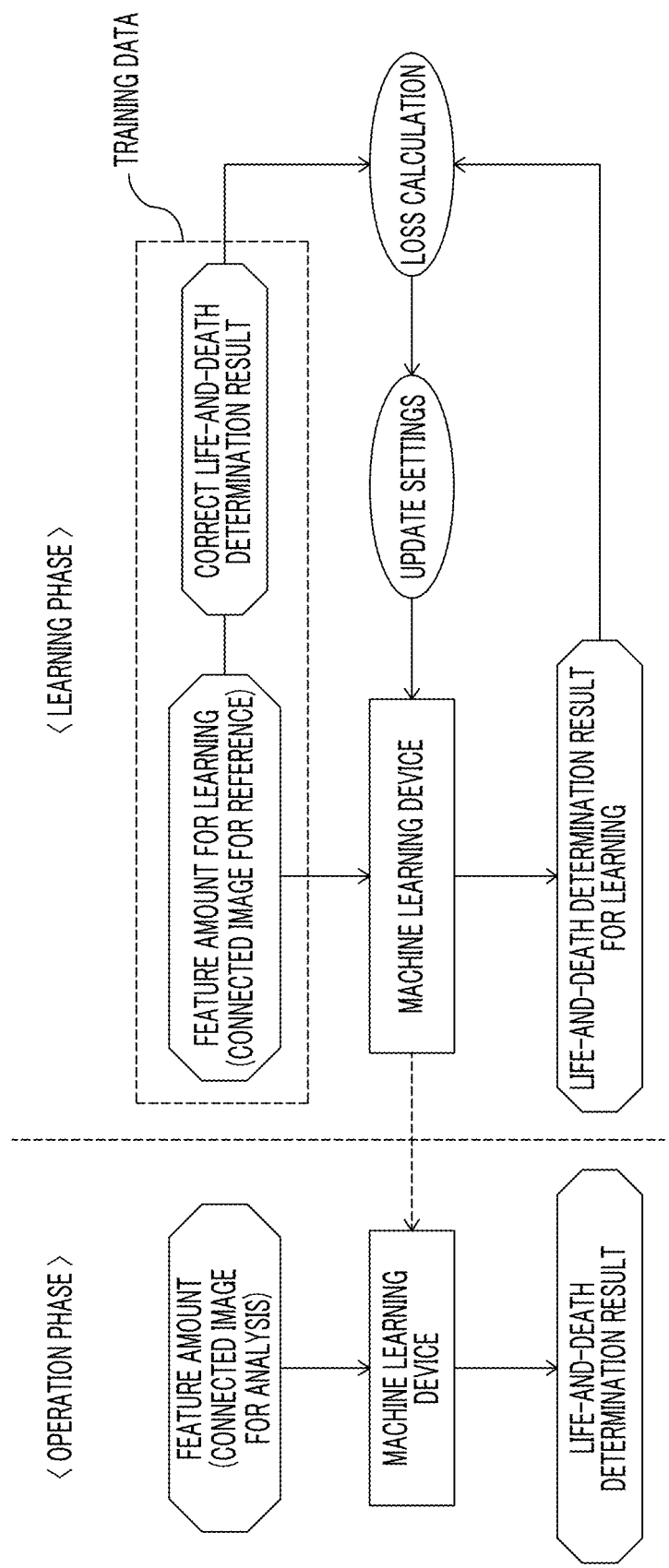
FIG. 7 is a schematic diagram illustrating an example of a process of a machine learning device in a learning phase and an operation phase.

As illustrated in FIG. 7, in a learning phase, the machine learning device is given training data and then trained. The training data is a set of the feature amount of the known connected image for reference of the cell (hereinafter, sometimes referred to as a "feature amount for learning") and the result of determining whether or not the cell is the living cell corresponding to the feature amount for learning (hereinafter, sometimes referred to as a "correct life-and-death determination result").

In the learning phase, the feature amount for learning is input to the machine learning device. The machine learning device outputs a life-and-death determination result for learning with respect to the feature amount for learning. The loss calculation of the machine learning device using a loss function is performed on the basis of the life-and-death determination result for learning and the correct life-and-death determination result. Then, update settings of various coefficients of the machine learning device are made according to the result of the loss calculation, and the machine learning device is updated according to the update settings.

In the learning phase of the machine learning device, the series of processes of the input of the feature amount for learning to the machine learning device, the output of the life-and-death determination result for learning from the machine learning device, the loss calculation, the update setting, and the update of the machine learning device is repeated performed while the training data is being exchanged. The repetition of the series of processes is ended in a case in which the prediction accuracy of the life-and-death determination result for learning with respect to the correct life-and-death determination result has reached a predetermined set level. The machine learning device whose prediction accuracy has reached the set level is used in an operation phase and outputs the life-and-death determination result in response to the input of the feature amount of the connected image for analysis.

In the life-and-death determination step, it may be determined whether a plurality of cells in the cell suspension are alive or dead.

For example, a connected image for analysis is created for the plurality of cells in the cell suspension. Then, whether the cell is alive or dead may be determined on the basis of the feature amounts of these connected images for analysis, the feature amount of the known connected image for reference of the cell, and the result of determining whether or not the cell is the living cell.

In addition, for example, the connected images for analysis of the target cell and other substances (for example, other cells, red blood cells, and oil droplets) are created using the cell suspension including the target cell and other substances. Then, the identification of the target cell and the determination of whether the target cell is alive or dead may be performed at the same time on the basis of the feature amounts of these connected images for analysis, the feature amount of the known connected image for reference of the target cell, and the result of determining whether or not the target cell is the living cell.

Figure 8:
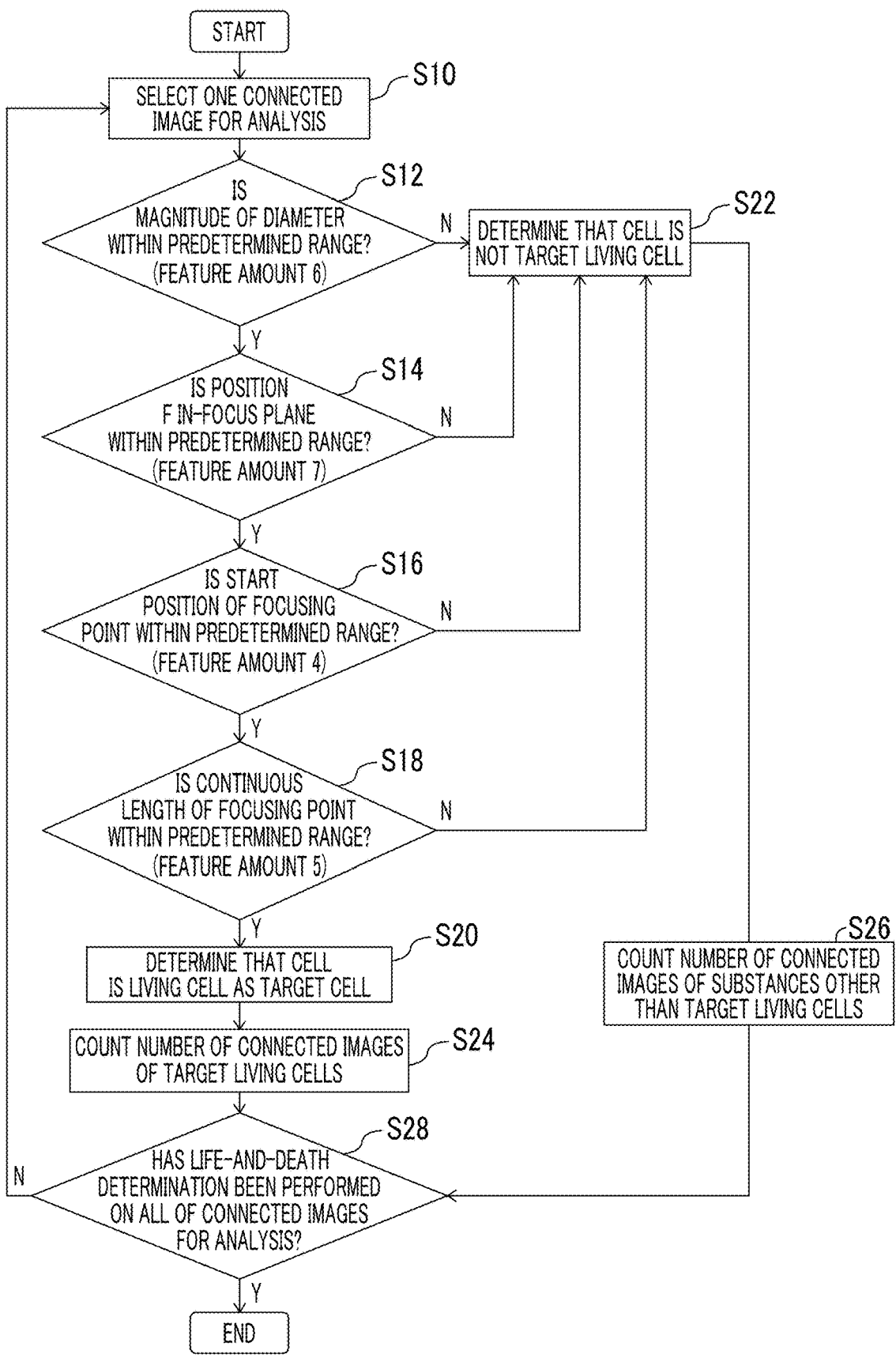
FIG. 8 is a flowchart illustrating an example of a life-and-death determination flow of a life-and-death determination step.

An example of a life-and-death determination flow of the life-and-death determination step will be described with reference to a flowchart illustrated in FIG. 8. The life-and-death determination flow illustrated in FIG. 8 is an example in which the target cell is identified using the feature amounts 4 to 7 and whether the target cell is alive or dead is determined using the feature amounts 4 and 5.

—Step S10—

One connected image for analysis is selected from a plurality of connected images for analysis (S10).

—Step S12—

It is determined whether or not the feature amount 6 (the magnitude of the diameter) of the connected image for analysis is within a predetermined range of the feature amount 6 (S12). In a case in which the feature amount 6 of the connected image for analysis is within the above-described range, it is determined that the cell is the target cell, and the process proceeds to the next step (S14).

In a case in which the feature amount 6 of the connected image for analysis is not within the above-described range, it is determined that the cell is not the target cell ($S_{22}$).

—Step S14—

It is determined whether or not the feature amount 7 (the position of the in-focus plane) of the connected image for analysis is within a predetermined range of the feature amount 7 (S14). In a case in which the feature amount 7 of the connected image for analysis is within the above-described range, it is determined that the cell is the target cell, and the process proceeds to the next step (S16).

In a case in which the feature amount 7 of the connected image for analysis is not within the above-described range, it is determined that the cell is not the target cell (S22).

—Step S16—

It is determined whether or not the feature amount 4 (the start position of the focusing point) of the connected image for analysis is within a predetermined range of the feature amount 4 (S16). In a case in which the feature amount 4 of the connected image for analysis is within the above-described range, it is determined that the cell is a living cell as the target cell (hereinafter, sometimes referred to as a "target living cell"), and the process proceeds to the next step (S18).

In a case in which the feature amount 4 of the connected image for analysis is not within the above-described range, it is determined that the cell is not the living cell as the target cell (S22).

—Step S18—

It is determined whether or not the feature amount 5 (the continuous length of the focusing point) of the connected image for analysis is within a predetermined range of the feature amount 5 (S18). In a case in which the feature amount 5 of the connected image for analysis is within the above-described range, it is determined that the cell is the living cell as the target cell (S20).

In a case in which the feature amount 5 of the connected image for analysis is not within the above-described range, it is determined that the cell is not the living cell as the target cell (S22).

—Step S20 and Step S22—

In a case in which it is determined that the cell is the living cell as the target cell (S20), the process proceeds to the next step (S24). In a case in which it is determined that the cell is not the living cell as the target cell (S22), the process proceeds to the next step (S26).

—Step S24—

The number of connected images in which the cell has been determined to be the living cell as the target cell is counted, and the process proceeds to the next step (S28).

—Step S26—

The number of connected images in which the cell has been determined not to be the living cell as the target cell is counted, and the process proceeds to the next step (S28).

—Step S28—

In a case in which there is a connected image for analysis in which whether the target cell is alive or dead has not been determined, the process returns to Step $S_{10}$. In a case in which whether the target cell is alive or dead has been determined for all of the connected images for analysis, the life-and-death determination flow is ended.

[Living Cell Concentration Determination Step]

The cell life-and-death determination method may include a step of determining the living cell concentration of the cells in the cell suspension on the basis of the result of determining whether the plurality of cells in the cell suspension are alive or dead (hereinafter, sometimes referred to as a "living cell concentration determination step").

In the present disclosure, the living cell concentration of the cells means the number of living cells per unit volume [cells/ml].

For example, the living cell concentration of the cells can be calculated as follows.

The cell suspension is accommodated in the holding container, a connected image for analysis is created for all of the cells (which may include substances (for example, other cells, red blood cells, and oil droplets) other than the target cell) present between the bottom of the holding container and the surface of the cell suspension in a randomly selected field of view, it is determined whether the cells are alive or dead, and the number of connected images for analysis in which the cell has been determined to be the living cell is used as the number of living cells. The number of living cells can be divided by the volume of the cell suspension used for measurement (that is, the product of the area of the field of view and the height of the cell suspension (the height from the bottom surface of the holding container to the liquid surface)) to calculate the living cell concentration of the cells in the cell suspension.

The living cell concentration of the cells can be understood to calculate the amount of diluent required, for example, in a case in which the cell suspension, which is a mother liquor, is diluted and used for cell culture. This makes it easy to adjust the cell suspension to a desired concentration and to perform seeding.

As described above, according to the cell life-and-death determination method of the present disclosure, it is possible to determine whether the cells are alive or dead and to calculate the living cell concentration of the cells.

[Cell Survival Rate Determination Step]

The cell life-and-death determination method may include a step of determining a cell survival rate of the cells in the cell suspension on the basis of the result of determining whether the plurality of cells in the cell suspension are alive or dead (hereinafter, sometimes referred to as a "cell survival rate determination step").

The cell survival rate is a value obtained by dividing the number of living cells by the total number of cells (the sum of the number of living cells and the number of dead cells).

The cell survival rate can be calculated by setting the number of connected images for analysis in which the cell has been determined to be the living cell (for example, Step $S_{24}$ in FIG. 8) as the number of living cells and by setting the total number of connected images for analysis (for example, Steps S24 and S26 in FIG. 8) as the total number of cells. In subculture and expansion culture, the cell suspension includes only one type of target cell. Therefore, the cell survival rate obtained in this case is the ratio of the target living cells to all of the target cells.

<Cell Life-and-Death Determination Device and Cell Life-and-Death Determination System>

A cell life-and-death determination device according to the present disclosure comprises: an image acquisition unit that acquires images of a cell captured in a plurality of focal planes including an in-focus plane of the cell in a direction opposite to a side on which the cell is irradiated with light; an image piece acquisition unit that acquires an image piece including a central portion and an outer peripheral portion of the cell from each of the images; a connected-image-for-analysis creation unit that connects the image pieces in an order of an imaging direction of the focal plane to create a connected image for analysis; a feature amount extraction unit that extracts a feature amount from the connected image for analysis; and a life-and-death determination unit that determines whether the cell is alive or dead on the basis of the feature amount of the connected image for analysis, a feature amount of a known connected image for reference of the cell, and a result of determining whether or not the cell is a living cell.

The life-and-death determination unit may be configured by a machine learning device.

The cell life-and-death determination device may comprise a living cell concentration determination unit that determines a living cell concentration of a plurality of cells in a cell suspension on the basis of a result of determining whether the cells in the cell suspension are alive or dead.

The cell life-and-death determination device may comprise a cell survival rate determination unit that determines a cell survival rate of the cells in the cell suspension on the basis of the result of determining whether the plurality of cells in the cell suspension are alive or dead.

The image acquisition unit, the image piece acquisition unit, the connected-image-for-analysis creation unit, the feature amount extraction unit, the life-and-death determination unit, the living cell concentration determination unit, and the cell survival rate determination unit in the cell life-and-death determination device correspond to an image acquisition step, an image piece acquisition step, a connected-image-for-analysis creation step, a feature amount extraction step, a life-and-death determination step, a living cell concentration determination step, and a cell survival rate determination step in a cell life-and-death determination method, respectively.

The cell life-and-death determination device may be operated as a cell life-and-death determination system comprising another device that acquires the images of the cell in a plurality of focal planes.

The cell life-and-death determination system according to the present disclosure comprises a light source that emits light, an imaging device that images cells, and a unit that changes a focal plane.

The unit that changes the focal plane is not particularly limited and may be, for example, a stage moving mechanism that moves a stage, on which a holding container holding the cell is placed, to change a distance between the cell and the imaging device. As illustrated in FIG. 1, for example, a cell life-and-death determination system 200 may comprise a light source 10 that irradiates the cell C with light, the imaging device 20 that images the cell C, the holding container 40 that holds the cell (cell suspension) C, the stage 30 (stage moving mechanism) that moves the holding container 40 to change the distance between the cell C and the imaging device 20, and the cell life-and-death determination device 100 according the present disclosure.

The unit that changes the focal plane may be an imaging device moving mechanism that moves the imaging device to change the distance between the cell and the imaging device.

In addition, the imaging device may comprise a liquid lens as the unit that changes the focal plane.

In another embodiment, the cell life-and-death determination system may not comprise the imaging device or the like and may comprise, for example, an external storage device in which the images of the cells are stored. In addition, the cell life-and-death determination device may acquire the image of the cells from the external storage device.

The cell life-and-death determination system may comprise an input device for inputting data and a display device for displaying, for example, the result of determining whether the cell is alive or dead. For example, a keyboard can be used as the input device. For example, a monitor can be used as the display device.

Hereinafter, the cell life-and-death determination device according to the present disclosure will be described in more detail, using the cell life-and-death determination system 200 illustrated in FIG. 1 as an example.

Figure 9:
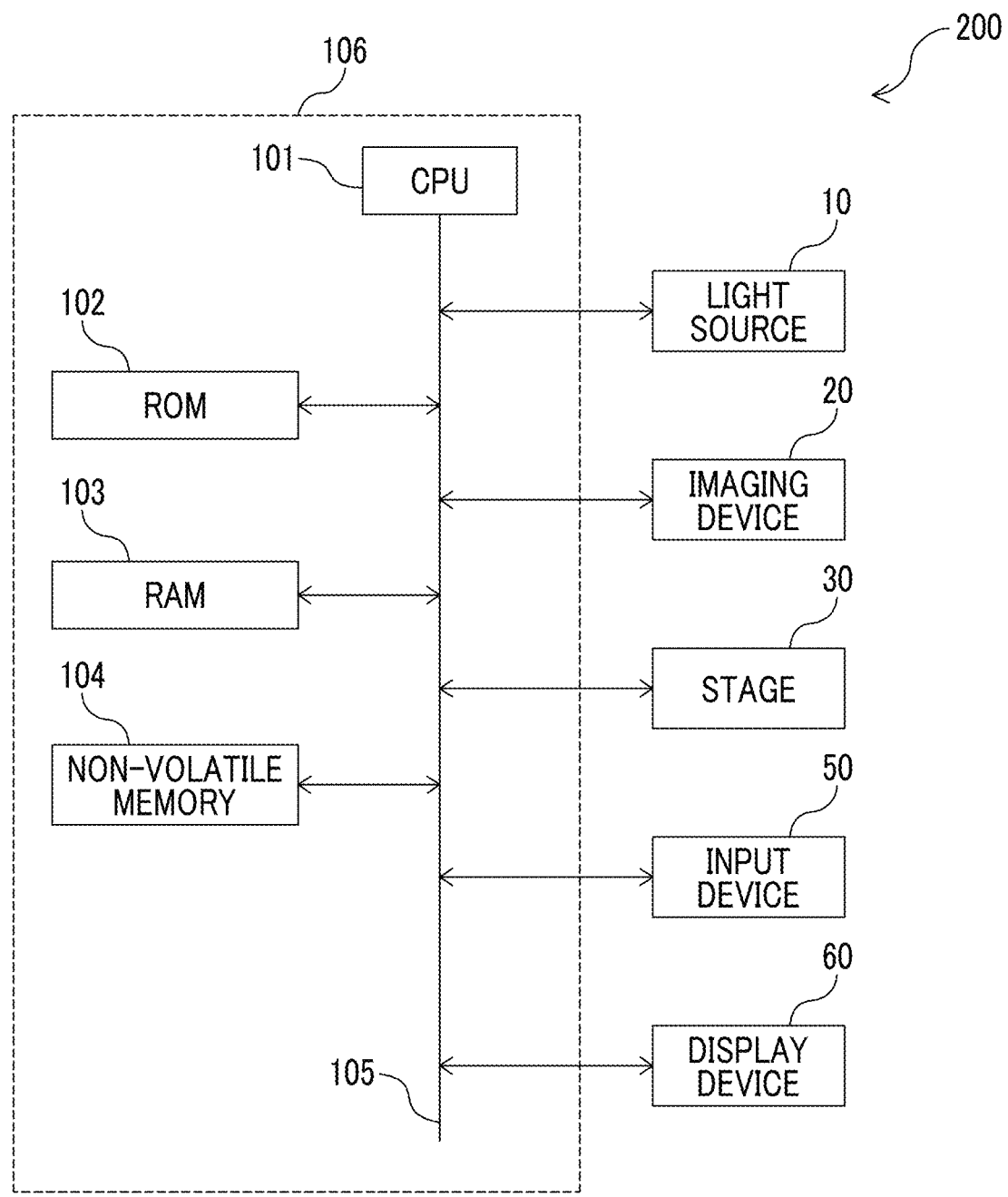
FIG. 9 is a block diagram illustrating an example of a control unit that constitutes a cell life-and-death determination device.

FIG. 9 is a block diagram illustrating an example of a control unit 106 constituting the cell life-and-death determination device 100 illustrated in FIG. 1. A central processing unit (CPU) 101 comprised in the control unit 106 is a processor that controls the overall operation of the cell life-and-death determination system 200. The CPU 101 reads a system program stored in a read only memory (ROM) 102 through a bus 105 and controls the entire cell life-and-death determination device 100 according to the system program. A random access memory (RAM) 103 temporarily stores, for example, temporary calculation data, data to be displayed on a display device 60, and various types of data input through an input device 50.

A non-volatile memory 104 stores, for example, data acquired from the light source 10, data acquired from the imaging device 20, data acquired from the stage 30, and data inputted from the input device 50, using a static random access memory (SRAM), a solid state drive (SSD), or the like which is backed up by a battery (not illustrated). For example, the data and the programs stored in the non-volatile memory 104 may be developed in the RAM 103 during use. In addition, for example, various algorithms required to analyze image data acquired from the imaging device 20 and system programs for performing other required processes are written in the ROM 102 in advance.

The result of determining whether the cell is alive or dead is output to the display device 60.

Figure 10:
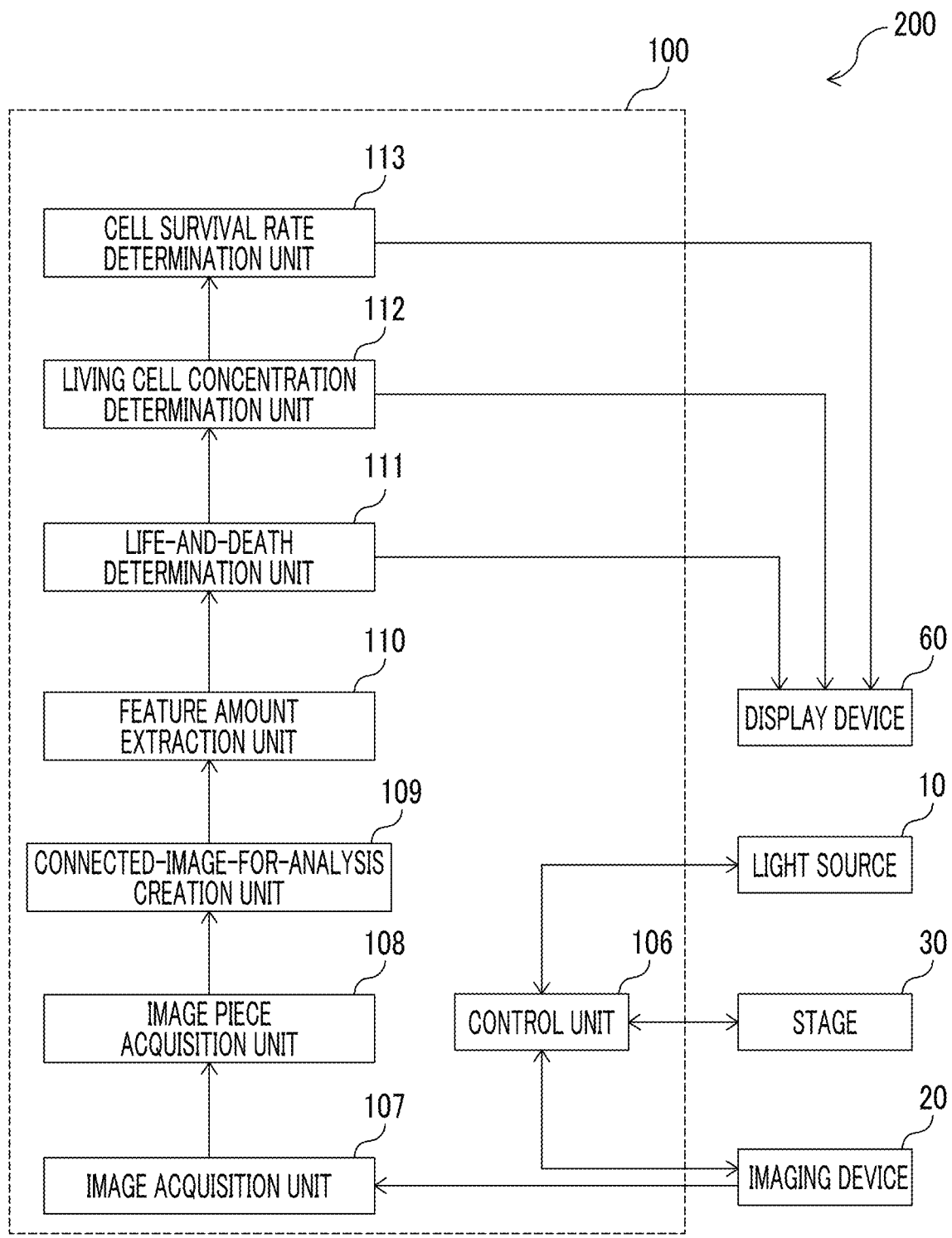
FIG. 10 is a block diagram illustrating an example of a process of the cell life-and-death determination device.

FIG. 10 is a block diagram illustrating an example of a process of the cell life-and-death determination device illustrated in FIG. 1. The CPU 101 comprised in the cell life-and-death determination device 100 illustrated in FIG. 1 executes the system program to control the operation of each unit of the cell life-and-death determination system 200, thereby implementing each functional block illustrated in FIG. 10.

The control unit 106 controls the light source 10, the imaging device 20, and the stage 30 on the basis of an imaging program stored in the non-volatile memory 104 such that the cell C is imaged. The control unit 106 turns on the light source 10 to irradiate the cell C with light and drives the stage 30 such that the holding container 40 holding the cell (cell suspension) C is moved to change the focal plane. After moving the stage 30 to a predetermined focal plane, the control unit 106 issues a command to perform an imaging operation to the imaging device 20. The control unit 106 images the cell in a plurality of focal planes including the in-focus plane of the cell in the direction opposite to the side on which the cell is irradiated with the light according to the imaging program.

Further, in another embodiment, in a case in which the cell life-and-death determination system does not comprise the imaging device or the like and the images of the cells are acquired from the external storage device in which the images of the cells are stored, the control unit 106 and the imaging program are not necessary.

An image acquisition unit 107 acquires the image of the cell captured by the imaging device 20. For the image of the cell acquired by the image acquisition unit 107, a plurality of images obtained by imaging one cell may be collectively managed as one set of image data groups.

An image piece acquisition unit 108 performs image processing on the image of the cell acquired by the image acquisition unit 107 and acquires an image piece including a central portion and an outer peripheral portion of the cell from the image of the cell. For the image piece acquired by the image piece acquisition unit 108, a plurality of image pieces obtained by imaging one cell may be collectively managed as one set of image piece data groups.

A connected-image-for-analysis creation unit 109 performs image processing on the image pieces obtained by the image piece acquisition unit 108 and connects the image pieces in the order of the imaging direction of the focal plane to create a connected image for analysis.

A feature amount extraction unit 110 performs image processing on the connected image for analysis obtained by the connected-image-for-analysis creation unit 109 to extract a feature amount from the connected image for analysis.

A life-and-death determination unit 111 determines whether the cell is alive or dead on the basis of the feature amount of the connected image for analysis extracted by the feature amount extraction unit 110 and a predetermined range of the feature amount. In another embodiment, the life-and-death determination unit 111 determines whether the cell is alive or dead on the basis of the feature amount of the connected image for analysis extracted by the feature amount extraction unit 110, the feature amount of the known connected image for reference of the cell, and the result of determining whether or not the cell is the living cell. The life-and-death determination unit 111 outputs the result of determining whether the cell is alive or dead, which has been generated by the determination, to the display device 60.

A living cell concentration determination unit 112 determines the living cell concentration of the cells on the basis of the result of determining whether the cell is alive or dead, that is, the number of connected images for analysis in which the cell has been determined to be the living cell. The living cell concentration determination unit 112 outputs the living cell concentration of the cells to the display device 60.

A cell survival rate determination unit 113 determines a cell survival rate on the basis of the result of determining whether the cell is alive or dead, that is, the number of connected images for analysis in which the cell has been determined to be the living cell and the total number of connected images for analysis. The cell survival rate determination unit 113 outputs the cell survival rate to the display device 60.

Other details are as described above in the cell life-and-death determination method.

As described above, it is possible to determine whether the cells are alive or dead and to calculate the living cell concentration of the cells, using the cell life-and-death determination device according to the present disclosure.

The disclosure of JP2021-076026 filed on Apr. 28, 2021 is incorporated herein by reference in its entirety. All documents, patent applications, and technical standards disclosed in this specification are incorporated in this specification by reference such that the incorporation of each of the documents, the patent applications, and the technical standards by reference is specific and is as detailed as each of the documents, the patent applications, and the technical standards.

What is claimed is:

1. A cell life-and-death determination method comprising:
    acquiring images of a cell captured in a plurality of focal planes including an in-focus plane of the cell in a direction opposite to a side on which the cell is irradiated with light;
    acquiring an image piece including a central portion and an outer peripheral portion of the cell from each of the images;
    connecting the image pieces in an order of an imaging direction of the focal plane to create a connected image for analysis;
    extracting a feature amount from the connected image for analysis; and
    determining whether the cell is alive or dead on the basis of the feature amount of the connected image for analysis and a predetermined range of the feature amount.

2. The cell life-and-death determination method according to claim 1,
wherein the determining of whether the cell is alive or dead includes determining whether or not the cell is a target cell.

3. The cell life-and-death determination method according to claim 1,
wherein the determining of whether the cell is alive or dead is performed by a machine learning device on the basis of a feature amount of a known connected image for reference of the cell and a result of determining whether or not the cell is a living cell.

4. The cell life-and-death determination method according to claim 1,
wherein the feature amounts of the connected image for analysis include one or more feature amounts selected from a group consisting of a feature amount related to a lens effect of the cell, a feature amount related to an average refractive index of the cell, a feature amount related to a diameter of the cell, and a feature amount related to a specific gravity of the cell.

5. The cell life-and-death determination method according to claim 1,
wherein the determining of whether the cell is alive or dead is performed on a plurality of the cells in a cell suspension.

6. The cell life-and-death determination method according to claim 5, further comprising:
determining a living cell concentration of the cells in the cell suspension on the basis of a result of determining whether the cells are alive or dead.

7. The cell life-and-death determination method according to claim 5, further comprising:
determining a cell survival rate of the cells in the cell suspension on the basis of a result of determining whether the cells are alive or dead.

8. A cell life-and-death determination device comprising:
an image acquisition unit that acquires images of a cell captured in a plurality of focal planes including an in-focus plane of the cell in a direction opposite to a side on which the cell is irradiated with light;
an image piece acquisition unit that acquires an image piece including a central portion and an outer peripheral portion of the cell from each of the images;
a connected-image-for-analysis creation unit that connects the image pieces in an order of an imaging direction of the focal plane to create a connected image for analysis;
a feature amount extraction unit that extracts a feature amount from the connected image for analysis; and
a life-and-death determination unit that determines whether the cell is alive or dead on the basis of the feature amount of the connected image for analysis and a predetermined range of the feature amount.

9. The cell life-and-death determination device according to claim 8,
wherein the life-and-death determination unit is configured by a machine learning device and determines whether the cell is alive or dead on the basis of a feature amount of a known connected image for reference of the cell and a result of determining whether or not the cell is a living cell.

10. The cell life-and-death determination device according to claim 8, further comprising:
a living cell concentration determination unit that determines a living cell concentration of a plurality of the cells in a cell suspension on the basis of a result of determining whether the cells in the cell suspension are alive or dead.

11. The cell life-and-death determination device according to claim 10, further comprising:
a cell survival rate determination unit that determines a cell survival rate of the cells in the cell suspension on the basis of the result of determining whether the cells are alive or dead.

12. A cell life-and-death determination system comprising:
the cell life-and-death determination device according to claim 8;
a light source that emits the light;
an imaging device that images the cell; and
a unit that changes the focal plane.

13. The cell life-and-death determination system according to claim 12,
wherein the unit changing the focal plane is a stage moving mechanism that moves a stage, on which a holding container holding the cell is placed, to change a distance between the cell and the imaging device.

14. The cell life-and-death determination system according to claim 12,
wherein the unit changing the focal plane is an imaging device moving mechanism that moves the imaging device to change a distance between the cell and the imaging device.

15. The cell life-and-death determination system according to claim 12,
wherein the imaging device includes a liquid lens as the unit changing the focal plane.

* * * * *